(12) United States Patent
Yoon et al.

(10) Patent No.: US 8,747,776 B2
(45) Date of Patent: Jun. 10, 2014

(54) MICROFLUIDIC PLATFORM FOR DISCRETE CELL ASSAY

(75) Inventors: Euisik Yoon, Superior Township, MI (US); Kim Young-Ji, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 13/504,830

(22) PCT Filed: Oct. 27, 2010

(86) PCT No.: PCT/US2010/054257
§ 371 (c)(1),
(2), (4) Date: Aug. 20, 2012

(87) PCT Pub. No.: WO2011/056643
PCT Pub. Date: May 12, 2011

(65) Prior Publication Data
US 2013/0130301 A1 May 23, 2013

Related U.S. Application Data

(60) Provisional application No. 61/255,243, filed on Oct. 27, 2009.

(51) Int. Cl.
*B01L 3/00* (2006.01)

(52) U.S. Cl.
USPC ........................................................ 422/502

(58) Field of Classification Search
USPC ........................................................ 422/502
See application file for complete search history.

(56) References Cited

U.S. PATENT DOCUMENTS

| | | | |
|---|---|---|---|
| 2001/0055812 A1* | 12/2001 | Mian et al. ...................... | 436/45 |
| 2005/0272039 A1 | 12/2005 | Yasuda | |
| 2007/0031819 A1* | 2/2007 | Koschwanez et al. ............ | 435/4 |
| 2008/0241843 A1* | 10/2008 | Zare et al. .......................... | 435/6 |
| 2009/0253181 A1 | 10/2009 | Vangbo et al. | |
| 2013/0005585 A1* | 1/2013 | Anderson et al. ................. | 506/2 |
| 2013/0078163 A1* | 3/2013 | Chung et al. .................. | 422/502 |

FOREIGN PATENT DOCUMENTS

| | | |
|---|---|---|
| WO | WO2004018618 | 3/2004 |
| WO | WO2007136799 | 11/2007 |

OTHER PUBLICATIONS

Chung et al., Highly Efficient Single Cell Capturing in Microwell Array Using Hydrodynamic Guiding Structures, Oct. 12-16, 2008, Twelfth International Conference on Miniaturized Systems for Chemistry and Life Sciences, p. 477-479.*

International Search Report for PCT/US2010/054257, Jun. 24 2011, 3 pages.

Written Opinion for PCT/US2010/054257, Jun. 24, 2011, 6 pages.

Young-Ji, Kim, et al. "Microfluidic Array Chip for Single-Cell Isolation Using Two-Way Pneumatic Actuation", MEMS 2008, Tucson, AZ, Jan. 13-17, 2008, pp. 14-17.

* cited by examiner

*Primary Examiner* — Lore Jarrett
(74) *Attorney, Agent, or Firm* — Reising Ethington P.C.

(57) ABSTRACT

A microfluidic chamber for use in individual cell assays. The microfluidic chamber includes a cell microchamber having an interior region and front and rear valves, each of which are separately controllable so that they can be selectively opened and closed to thereby permit the transference of an individual cell into and out of the interior region. Cell secretion and contact interaction studies can be carried out using the microchambers, with the valves permitting either complete isolation or perfusion media flow through the microchambers. An internal perfusion wall can be included to partition the microchamber for non-contact perfusion studies of secretion interactions between cells.

17 Claims, 12 Drawing Sheets

(a) Gap open (b) Gap closed

MICROFLUIDIC PLATFORM FOR DISCRETE CELL ASSAY

TECHNICAL FIELD

This invention relates generally to microfluidic platforms for cell assays and to methods for single cell assays and for investigating cell signaling.

BACKGROUND OF THE INVENTION

Cell signaling is a part of a complex system of communication that governs basic cellular activities and coordinates cell action. The ability of cells to perceive and correctly respond to their microenvironment is the basis of development, tissue repair and immunity as well as normal tissue homeostasis. Errors in these crucial functions are responsible for diseases such as cancer, autoimmunity and diabetes, and due to the immense role that cell signaling plays, understanding it will provide the cornerstone in understanding diseases and their treatments. Moreover, a cell is capable of sending and receiving chemical signals from other cells, and usually interacts with other cells to achieve coordinated functions rather than exist as a single-cell in its own microenvironment. Therefore, the ability to qualify the cell signaling events is very important for understanding cellular responses.

Modeling of these complex processes will integrate experimental data on the distinct spatial-temporal dynamics of signaling from different cellular compartments and provides new insight into the connection between external stimuli and the signaling outcome in terms of gene expression responses, phenotype response and others. However, large sets of experimental data with the self-consistent and dynamic measures of protein activities are rare in utilizing conventional methods due to the cumbersome and complex nature of the experiments that are required.

One of the possible reasons for these predicaments is related to cellular heterogeneity. In recent studies on the cellular analyses, it has been observed that cells even in genetically identical cell populations under the same environmental conditions exhibit some degrees of variation. Therefore, the information obtained on the cell population level, which is based on the basis of averaged measurements of large group of cells can overlook very important observations or even lead to incorrect results. For this reason, there have been growing interests in single-cell assays to understand single-cell behavior more accurately. Also, cell-cell interactions leading to tissue development involve a small number of cells. So, more pertinent information could be obtained from single-cell level analyses. However, it can be difficult to perform single-cell level analyses using traditional tools because of its labor intensive and low throughput nature, while microfluidic approaches allow more precise control of cell positioning and reagent introduction in analyzing single-cells.

The inventors' earlier work includes the design, fabrication, and testing of a microfluidic chip array containing a plurality of microfluidic chambers each of which comprises a disc-shaped cell chamber that is formed with an initial gap of 5 μm from the underlying substrate to allow a flow stream into and out of the chamber. The chamber can be moved up or down by pneumatic activation using an air chamber that overlies the entire chamber. A cell capture site is formed in the chamber sidewall upstream of the flow and is used to trap an individual cell as the fluid stream moves over the substrate underneath the cell chamber. To load the cell, the air chamber is partially evacuated which, due to the flexibility of the chamber upper wall, enables the 5 μm to be increased large enough to allow the captured cell to move with the flow stream into the space under the now-lifted cell chamber. Thereafter, the air chamber is positively pressurized to push the cell chamber down onto the substrate to thereby completely isolate the cell within the interior region formed by the cell chamber and substrate.

This design, while allowing individual cell capture and assaying, is not designed to permit the introduction into the cell chamber of multiple cells. Thus, it does not permit studying of cell-to-cell interactions which could otherwise be useful in order to elucidate cellular processes such as stem cell proliferation and differentiation. Some recent studies have addressed this problem by allowing observation of single cell pairs in close proximity; however, these studies did not distinguish whether the interaction was induced by secretion or contact from other cells. Also, trapping of the cells within the chamber when it is lifted up to admit the cell can be problematic since the cell can move past the space under the chamber before it is closed or possibly become lodged between the cell chamber sidewall and substrate.

SUMMARY OF THE INVENTION

In accordance with an embodiment of the invention, there is provided a microfluidic chamber for use in individual cell assays. The microfluidic chamber includes a cell microchamber having an interior region and front and rear valves, with each of the valves being separately controllable so as to selectively open and close to thereby permit the transference of an individual cell into and out of the interior region. In accordance with another embodiment of the invention, there is provided a cell assay method using this microfluidic chamber, comprising the steps of: flowing fluid through the microchamber while the front and rear valves are in a neutral position that permits fluid flow through the microchamber and prevents cell transference into or out of the microchamber; capturing an individual cell at the front valve during fluid flow through the microchamber while the front valve is in the neutral position; admitting the individual cell into the interior region of the microchamber by opening the front valve during the fluid flow while maintaining the rear valve in the neutral position; and conducting a cell assay using the individual cell while the front and rear valves are set to either the neutral or closed position.

In accordance with another embodiment of the invention, there is provided a microfluidic chamber that includes a substrate, a chamber upper wall spaced from the substrate and at least partially defining an interior region, a chamber sidewall structure including at least one sidewall extending downwardly from the upper wall toward the substrate so as to at least partially define the interior region, and front and rear valves that permit fluid and cell entry into and exit out of the interior region, respectively. The chamber upper wall and chamber sidewall structure together comprising a cell microchamber attached to the substrate. The front valve comprises a first actuator and a first section of the sidewall structure located at a fluid entry point for the microchamber. The rear valve comprises a second actuator and a second section of the sidewall structure located at a fluid exit point for the microchamber. Each of the valves are controlled via its associated actuator to permit the valves to be switched between open, neutral, and closed positions, with the neutral position for each valve permitting fluid flow through the valve while preventing cell transference through the valve, the open position for each valve permitting fluid flow and cell transference through the valve, and the closed position preventing both fluid flow and cell transference through the valve.

In accordance with yet another embodiment of the invention, there is provided a cell loading method for use in cell assays, comprising the step of capturing a plurality of individual cells in a microchamber by sequentially admitting individual cells into the microchamber while preventing any other existing cells in the microchamber from escaping.

BRIEF DESCRIPTION OF THE DRAWINGS

Preferred exemplary embodiments of the invention will hereinafter be described in conjunction with the appended drawings, wherein like designations denote like elements, and wherein.

DETAILED DESCRIPTION OF THE PREFERRED EMBODIMENTS

Described below are embodiments of a microfluidic device and method for analyzing cell signaling and cell-cell interactions which can be done in single-cell resolution. As will become apparent from the description below, the illustrated microfluidic chamber permits (1) controllable cell loading at single-cell resolution, (2) the ability to isolate individual cells or small groups of cells together in close proximity in a microenvironment, and (3) biological assays to examine not only single-cell culture assays, but also the effect of cell-cell interactions by contact and/or via secreted soluble factors. The disclosed microchamber designs are also scalable to permit highly parallel assays of individual cells or individual groups of cells.

Figure 1:
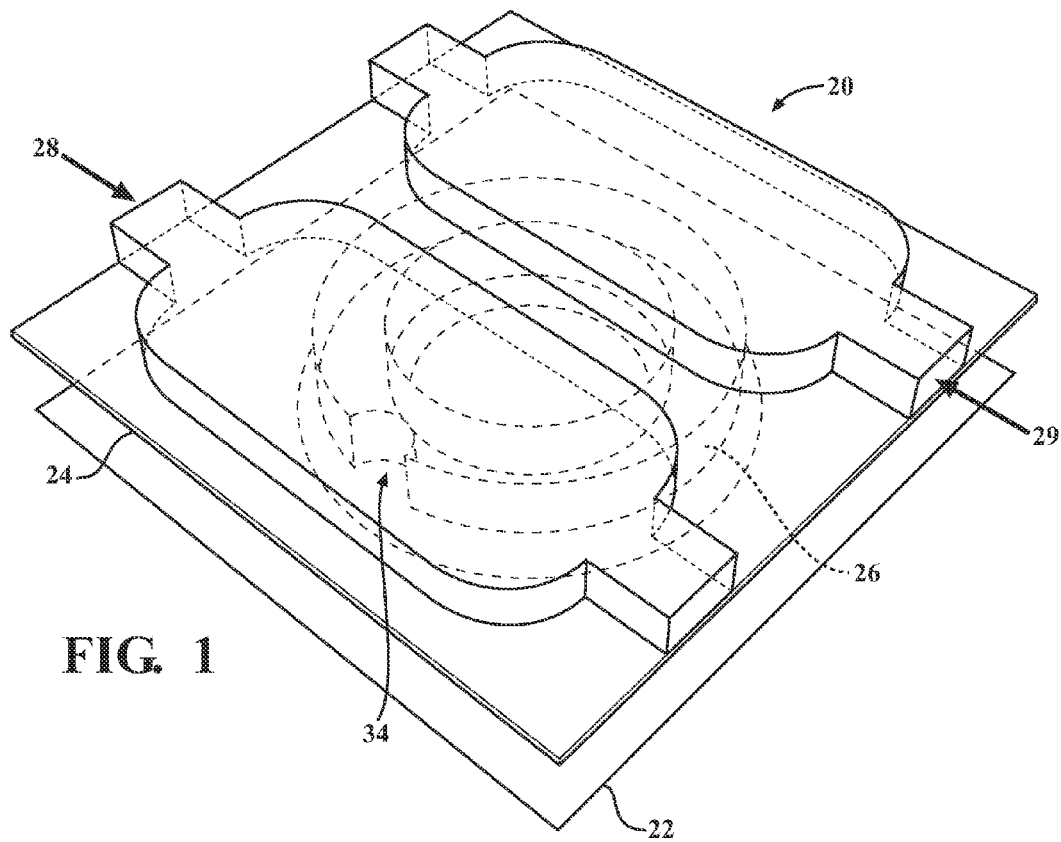
FIG. 1 is a three-dimensional partially transparent perspective view of an embodiment of a microchamber constructed in accordance with the present invention.
Figure 2:
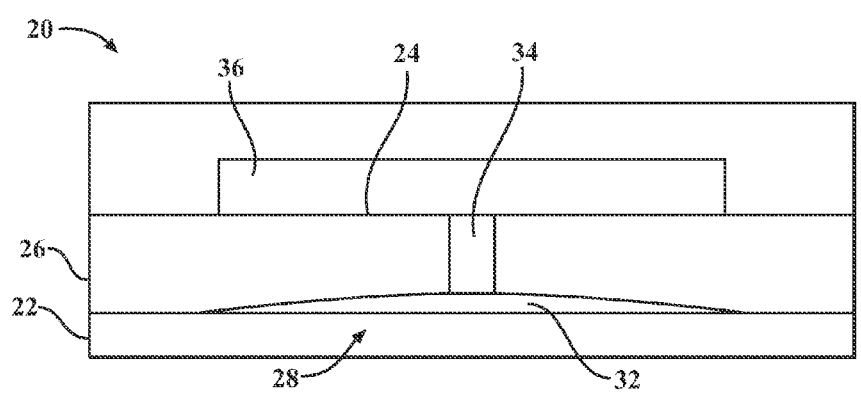
FIG. 2 is an elevational view of the microchamber of FIG. 1 showing its front valve and tapered opening.
Figure 3:
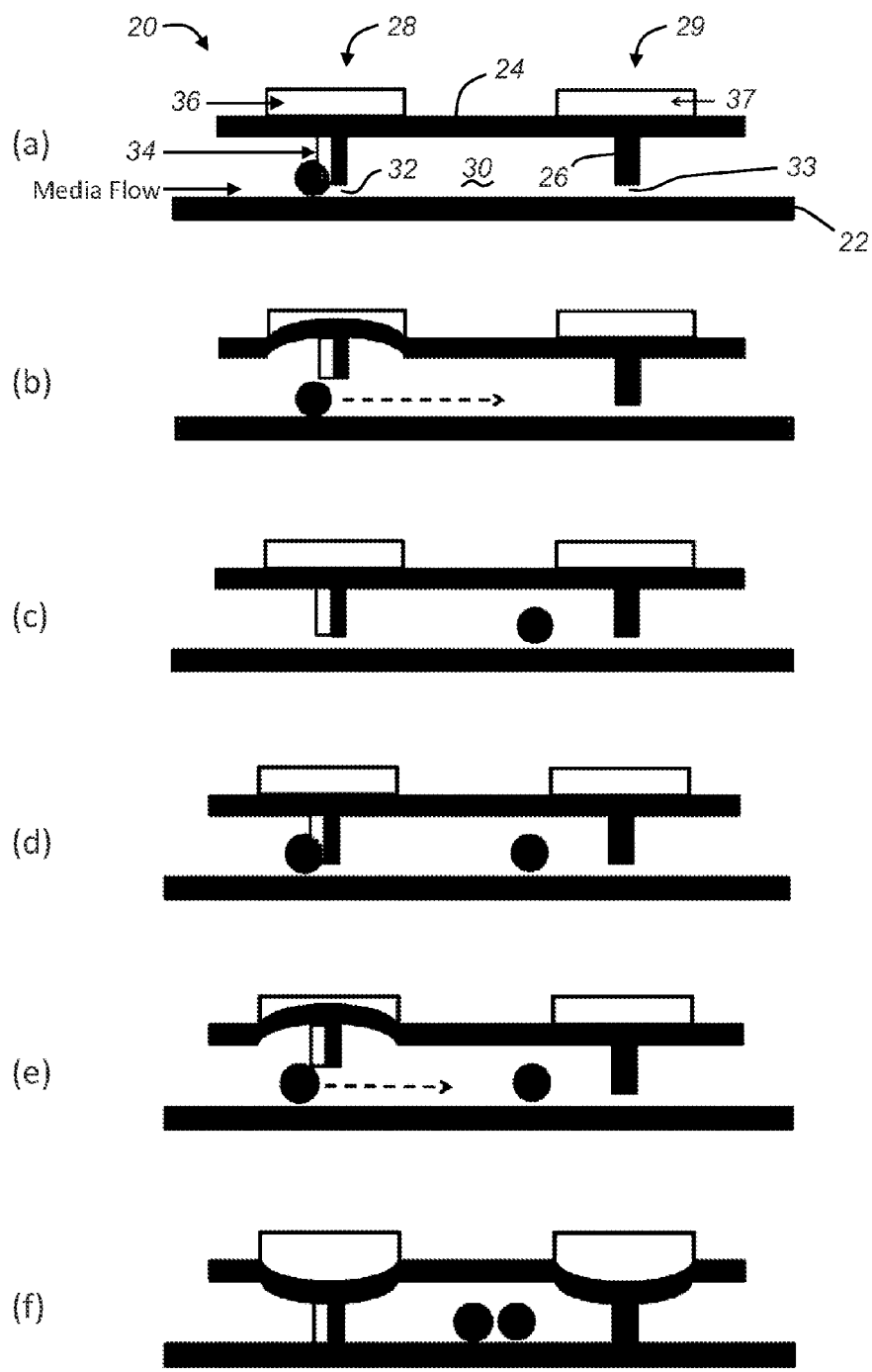
FIG. 3 depicts a sequential cell loading process for introducing individual cells into the microchamber of FIG. 1.

FIGS. 1-3 depict a microfluidic device having a single microchamber 20 that generally comprises a substrate 22, chamber upper wall 24, a chamber sidewall structure 26 that extends downwardly from the upper wall 24 towards the substrate 22, and front and rear valves 28, 29 that control the injection and extraction of cells and perfusion media into and out of the interior region 30 of the microchamber 20. In the embodiment shown in FIGS. 1-3, the chamber sidewall structure 26 comprises a single annular sidewall, although it will be appreciated that polygonal and other shaped sidewall structures can be used. As indicated in the elevation view of the front valve in FIG. 2, the sidewall structure 26 extends from the upper wall 24 to the substrate 22 except at the valve 28 where it forms a tapered opening 32 that has a gap of about 5 μm at the maximum height of the opening 32 at the center of the valve. This gap varies from the maximum spacing at the center of the valve 28 down to zero at opposite ends of the valve where the sidewall 26 meets the substrate 22. As will be discussed below, operation of the valve 28 permits this gap to be increased, so as to admit cells into the interior 30 of the microchamber 20, or decreased down to zero to thereby seal the microchamber 20 and provide complete environmental isolation of the cell(s) within the chamber. Although the front valve 28 is shown in FIG. 2, the rear valve 29 can have the same construction so as to include its own opening 33 through which cells can be released from the microchamber 20. This initial gap in the openings 32, 33 of the valves permits the flow of media through the microchamber while preventing cell transference either into or out of the interior region 30 of the chamber. A cell capture site 34 is provided at the front valve 28 upstream of the media flow so that by inserting cells into the flow stream, the cell capture site 34 can trap an individual cell while the fluid is flowing into the opening 32. Then, by activating the front valve 28 to fully open it, the cell can then be drawn by the flow stream into the interior region 30 of the chamber. The valve 28 can then be returned to its initial state (partially opened) to permit perfusion or can be closed completely along with the rear valve 29 to isolate the cell.

Thus, it will be appreciated that each valve provides a tri-state operation that includes a closed position, neutral (partially opened) position, and open position, with the neutral position for each valve permitting fluid flow through the valve while preventing cell transference through the valve, the open position for each valve permitting fluid flow and cell transference through the valve, and the closed position preventing both fluid flow and cell transference through the valve. Preferably, the microchamber 20 is made from a flexible material such that each valve 28, 29 can be pneumatically controlled via an actuator in the form of a respective fluid chamber 36, 37 positioned above the section of sidewall 26 located at its associated tapered opening 32, 33; see, for example, the front valve 28 shown in FIG. 2. The microchamber 20 is constructed such that the valves 28, 29 are in their neutral position when the microchamber is in a relaxed state; that is, when each valve's activating fluid chamber is neither pressurized nor partially evacuated. Then, by partially evacuating the fluid chamber, the chamber sidewall is drawn upwardly thereby increasing the gap at the valve opening to a size sufficient to admit a cell into the microchamber. Or, by applying a positive pressure to the fluid chamber, the chamber sidewall is forced downward into sealing engagement with the substrate.

This operation of the valves to sequentially capture two individual cells is shown in FIG. 3. The first step is to flow fluid containing injected cells across the substrate 22 while maintaining the valves 28, 29 in their neutral position. The results in the fluid flowing through the microchamber 20 such that an injected cell is trapped at the capturing site 34 during the flow. This shown at (a) in FIG. 3. Then, at (b), the front valve 28 is actuated to its open position which permits the trapped cell to move into the interior region 30 of the chamber under the drag force of the fluid flow. This is done while maintaining the rear valve 29 in it is neutral position. Then, at (c), the front valve 28 is returned to its neutral position. Again, this valve activation is carried out pneumatically using the pneumatic (or air) chamber 36 shown in FIG. 3. To capture a second cell in the microchamber, this process is repeated, as shown at (d) and (e) of FIG. 3. Additional cells can be inserted by iteratively repeating these steps. Finally, if desired for a particular cell study, both valves 28, 29 can be actuated to close them for complete isolation of the cells. This allows accumulation of secreted growth factors from cells cultured inside isolated microchamber. To remove the cell(s) from the chamber, the rear valve 29 is opened while providing fluid flow through the chamber with the front valve being held in either the neutral or open position. As will be appreciated, this microchamber design permits the sequential capturing of multiple cells in any desired number since one sequential operation captures a single cell at a time. The microchamber therefore makes possible a cell loading method that involves capturing a plurality of individual cells in a microchamber by sequentially admitting individual cells into the microchamber while preventing any other existing cells in the microchamber from escaping.

The fabrication process can be carried out using known techniques, such as by molding PDMS using SU-8 molds. For example, SU-8 can be patterned on a silicon wafer to form molds for the various microchamber structures (valves, air chambers, passages, etc.), and then PDMS poured into the molds to form the actual microchamber structures and/or spin coated to form complete layers. The molded microchamber structures can be bonded to a glass substrate using patterned platinum on the glass to prevent bonding of the PDMS to the glass where not desired. Examples of such fabrication techniques for other microfluidic devices are provided in Y.-J. Kim, J. Chung, H.-K. Lee and E. Yoon, "Microfluidic array chip for single-cell isolation using two-way pneumatic actuation," *Tech. Digest Papers MEMS '08 Conference*, pp. 14-17, 2008, and in K.-S. Yun and E. Yoon, "Micro/Nanofluidic Device for Single-Cell-Based Assay," *Biomedical Microdevices*, 7:1, 2005, pp. 35-40, the disclosures of which are hereby incorporated by reference.

Figure 4:
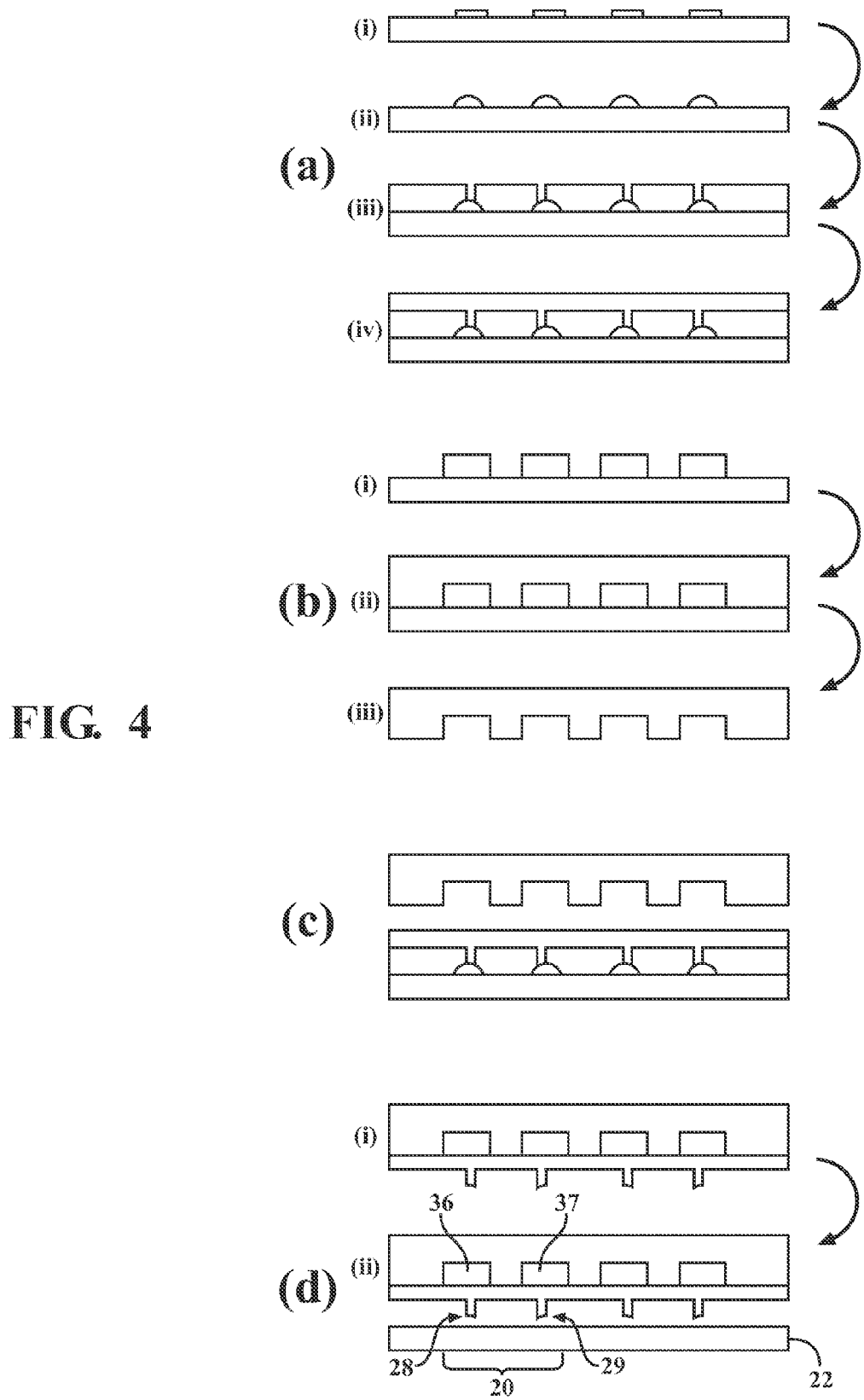
FIG. 4 shows the fabrication process including (a) microfluidic chamber formation, (b) air chamber (actuator) formation, (c) PDMS bonding between the microfluidic chamber and air chamber, and (d) final bonding between a glass slide substrate and the PDMS bonded chambers.

As one specific example, the overall fabrication process for two individual microchambers is shown in FIG. 4. For complete sealing of microchamber 20, the front and rear valve gaps shown in FIG. 2 located underneath chamber sidewall 26 can be patterned on silicon using standard positive photoresist (S1827), see FIG. 4(a)(i), and cured at 200° C. for 2 hours. By curing at high temperature, the rectangular shape of the photoresist patterns can be deformed into round shape—FIG. 4(a)(ii). These photoresist patterns are used to form the tapered opening in the front and rear valves—FIGS. 4(a)(iii)-(iv). 35 μm SU-8 patterning (FIG. 4(a)(iii)) is used and is intentionally mis-aligned with the rounded photoresist patterns, as shown in FIG. 4(a), to create the angled bottom edge of these tapered valve openings (shown in FIG. 4(d)) when PDMS coating and curing (50 μm) is carried out using the SU-8 mold. FIG. 4(b) shows the process of patterning 60 μm SU-8 (i), coating with PDMS (ii), and then PDMS cutting and release (iii) to create the valve actuation fluid chambers. After completing the fabrication of SU-8 master molds for both for microfluidic (FIG. 4(a)) and air (control) channel (FIG. 4(b)), the surface of master molds can be modified by self-assembled-monolayer of tridecafluoro-(1,1,2,2-tetrahydrooctyl)-1-trichlorosilane (United Chemical Technolo-gies) to prevent bonding between PDMS and the substrate and then are treated with spinning or pouring of uncured PDMS (Sylgard 184, company; 10:1 elastomer:crosslinker ratio). After curing the PDMS by baking at 80° C. (microfluidic channel) and 105° C. (air channel, higher temperature is for compensating PDMS shrinkage) for overnight, the thick air channel layer can be peeled off and punched for connection port. Then, it is aligned over the microchamber layer and bonded irreversibly with oxygen plasma treatment—FIG. 4(c). Then, all layers are peeled off (FIG. 4(d)(i)) and are bonded again on the glass slide substrate 22 (FIG. 4(d)(ii)).

As will be appreciated by those skilled in the art, this process can be used to produce an array of the microchambers 20 on the glass slide 22 with the front valves 28 of the different microchambers all interconnected with each other so that one pneumatic control source (not shown) can be used for simultaneous, parallel activation of the front valves 28. Similarly, the rear valves 29 can all be interconnected with each other so that they can be operated together. Alternatively, the valves can be configured to permit independent control of each valve of each microchamber or to permit simultaneous control of sub-groups of microchambers. Suitable chip layouts and pneumatic valve control switching for carrying out these different embodiments is within the level of skill of those in the art.

Figure 5:
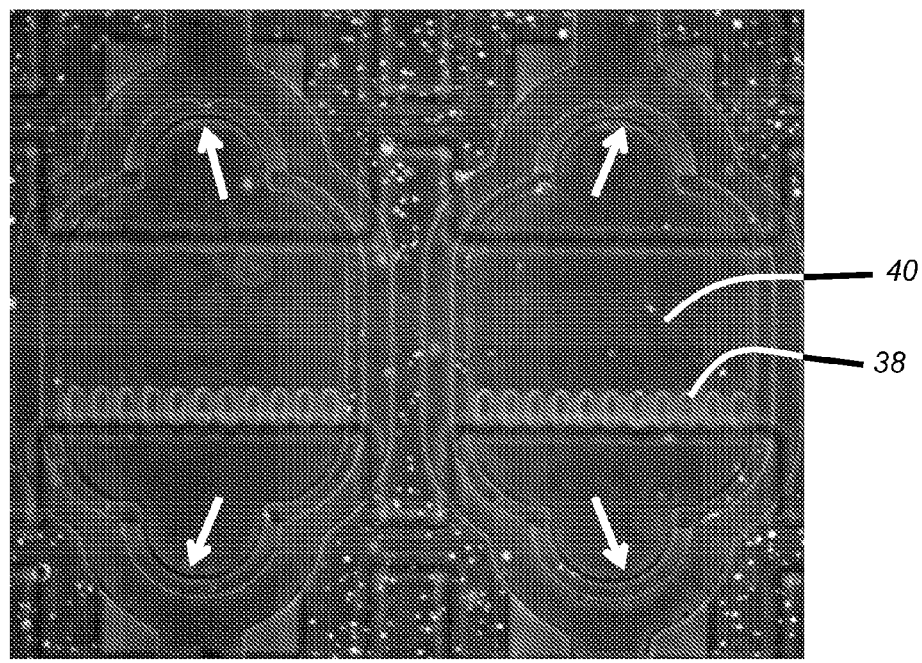
FIG. 5 is an image of a pair of fabricated microchambers, showing the operation of chamber actuation: (a) valves open, chamber is connected with main flow, (b) valves closed, border line has disappeared and the microchamber is completely isolated with ambient environment.
Figure 5:
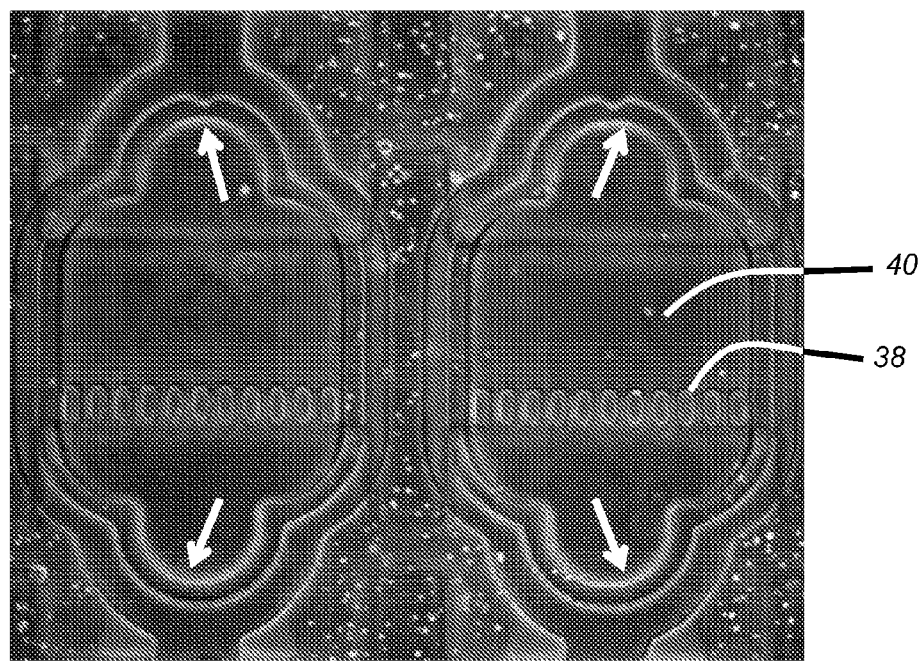

For the demonstration of microchamber isolation, a microfluidic chip was designed and fabricated having an array of microchambers. A plan view of two of the microchambers of this fabricated chip are shown in the photograph of FIG. 5. As pictured therein, each microchamber has a plan view shape comprising a rounded rectangular area rather than the circular one shown in FIGS. 1-3. The front and rear valves at each end of the rectangular chamber comprise semi-circular extensions of the microchamber having a tapered neutral position opening similar to that shown in FIG. 2, with the tapered opening having a maximum (neutral opening) height of 5 μm at the center of the semicircle. As in FIG. 2, the opening height tapers down to zero at the opposite ends of the semicircle. Photograph (a) in FIG. 5 depicts the valves in their neutral position in which the gap at the valves is open, and this is indicated by the arrows. In photograph (b), the valves are closed and this is visually evident by the lightened margins of the valves. Apart from the chamber and valve shape differences, the micro chambers of FIG. 5 also include an internal cell capture structure 38 within the interior region at a location between the front and rear valves. This cell capture structure 38 can have a net-like structure that permits fluid flow through the structure, but that prevents movement of individual cells past the structure. This helps collocate the cells within the structure in a middle region 40 of the chamber volume. For release of the cells, the cell capture structure can be operated with the rear valve to lift out of the way, or can have its own valve actuation, or a reverse flow through the microchamber can be used to release and remove the cells through the front valve.

For testing, the microfluidic chip was placed on a microscope and its pneumatic ports for the front and rear valves were connected with hand-made pneumatic actuation system with miniature pneumatic solenoid valves (ten millimeter miniature valves available from Numatech Inc., of Highland, Mich. USA) controlled by Lab-View Software™. The developed system can switch one or more valves separately in the chip between atmospheric pressure (open state) and 20 psi (closed state) as shown in FIG. 5. Isolation of the individual microchambers was successfully demonstrated and it was observed that there was no diffusion through microchambers at least for 4 hours.

Figure 6:
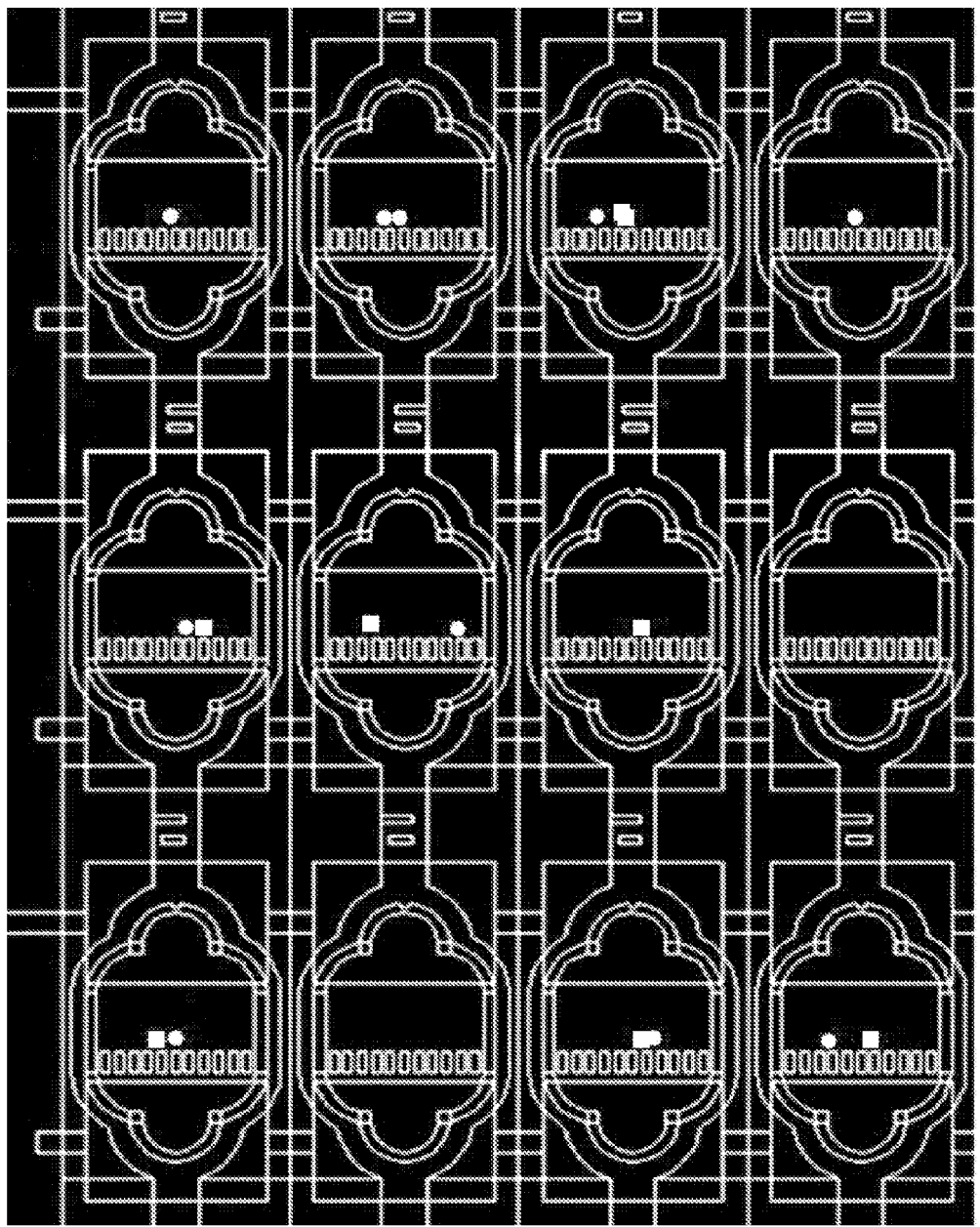
FIG. 6 is an altered fluorescence image of a portion of an array of microchambers formed on a single chip, showing the results of cell pairing microchamber loading according to the process of FIG. 3.

FIG. 6 is a contrast-enhanced fluorescence image of a portion of the array of microchambers on the fabricated chip showing a portion of the results of 2-cell pairing by loading PC3 cells and C2C12 cells fluorescently labeled in the original image with GFP (Green) and DsRed (Red), respectively. The image has been contrast enhanced for improved reproducibility and altered to mark the green cells with circles and the red cells with squares. Using the cell loading steps described above, 2 cell capture efficiency (i.e., the percentage of microchambers occupied with 2 different cell types) of up to 61% was obtained.

Figure 7:
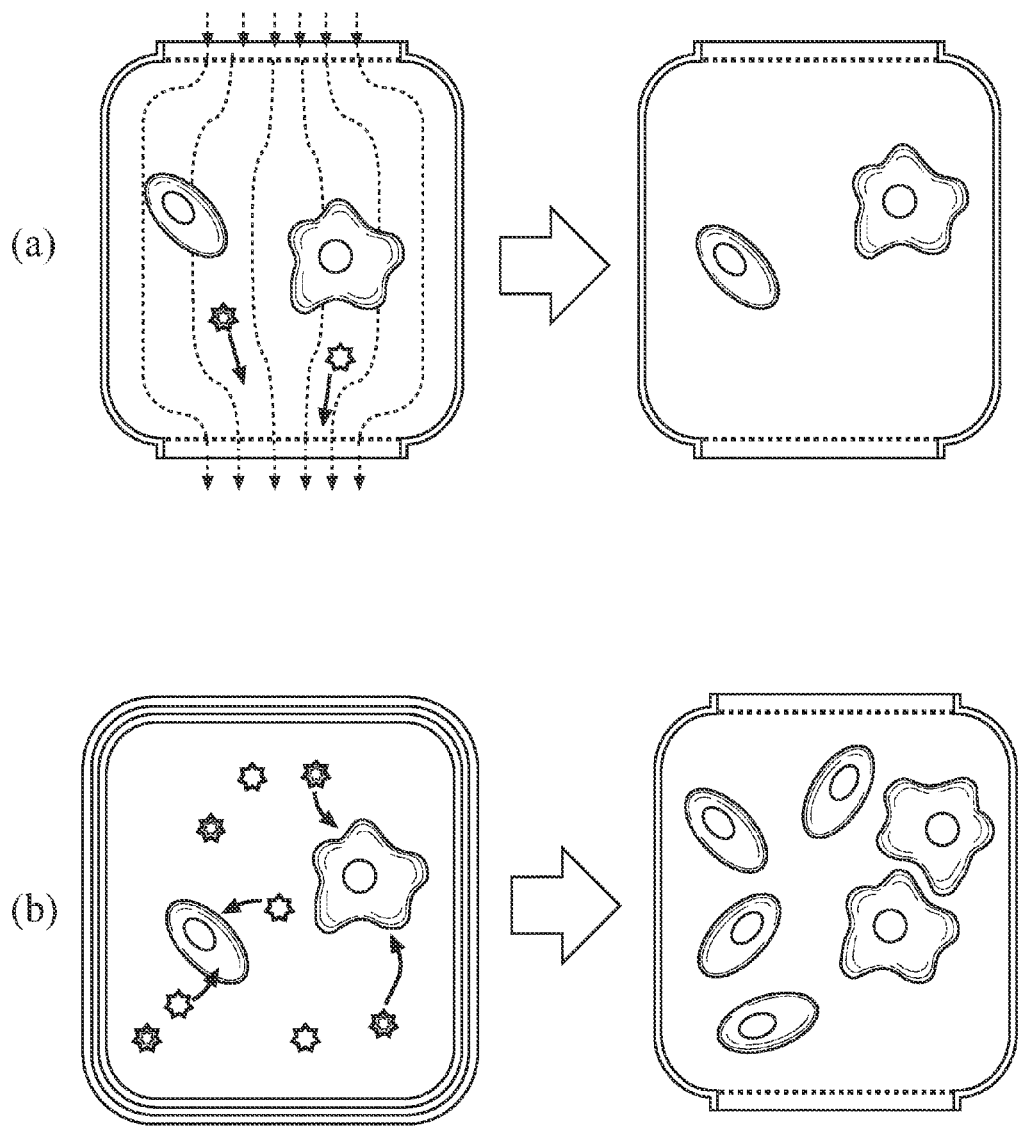
FIG. 7 is a diagram depicting the impact on cell interaction between microchamber perfusion and microchamber isolation of the cells.

Testing of cell interaction was also conducted. This involved first using the cell types C2C12 (Myoblast) and PC3 (Prostate Cancer). Prostate cancer cells have been observed to secrete various growth factors including VEGF (Vascular endothelial growth factor) and bFGF (Basic fibroblast growth factor). Using the value of references, the concentration of VEGF secreted from single PC3 cell was reached to around 100 pg/ml in an hour in the microchamber. Media supplemented with VEGF (the order of a few tens of ng/ml) can enhance the proliferation of Myoblast significantly. However, in a typical perfusion condition, the enhanced proliferation will not be observed because secreted cell signals will be washed away as soon as they are secreted. This is shown diagrammatically at (a) in FIG. 7 where media flow washes away secreted factors as indicated by the arrows so that, after three days, the cells remain unchanged. The microchamber device disclosed herein can avoid this problem by providing microchamber isolation that allows secreted cell signals to diffuse into their own microenvironment and cells in the same chamber, so that isolated cells can communicate and affect each other's cellular response during isolation period. Thus, as indicated at (b) in FIG. 7 where, after three days of accumulating diffusible signals from the two trapped cells, proliferation of the cells is seen. Thus, soluble factor signaling can be studied down at an individual cell level.

Figure 8:
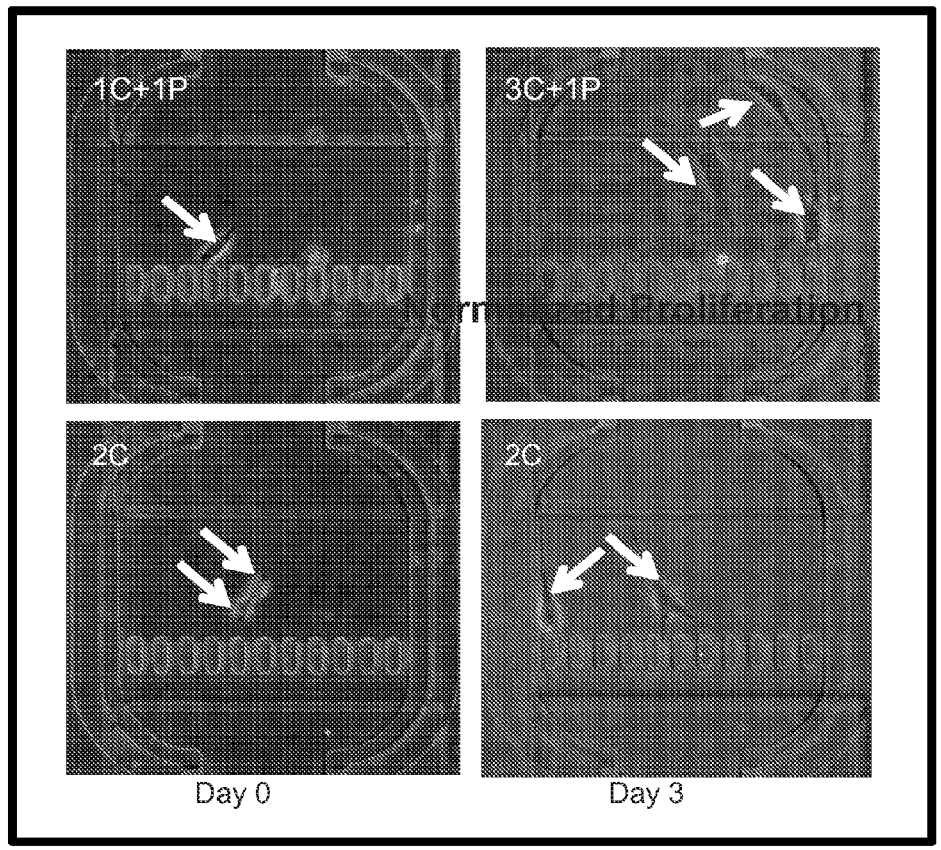
FIG. 8 depicts the results in a C2C12-PC3 culture with 3 hour isolation, showing that accumulated soluble factors for 3 hour in an isolated microchamber enhanced C2C12 proliferation.
Figure 8:
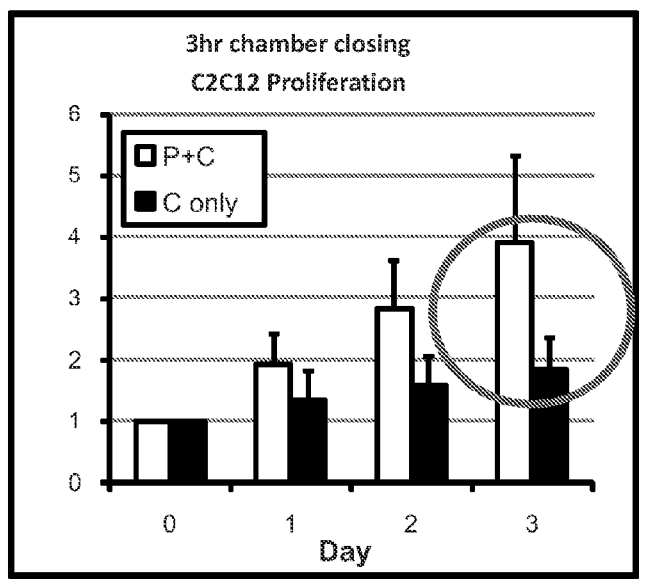
Figure 9:
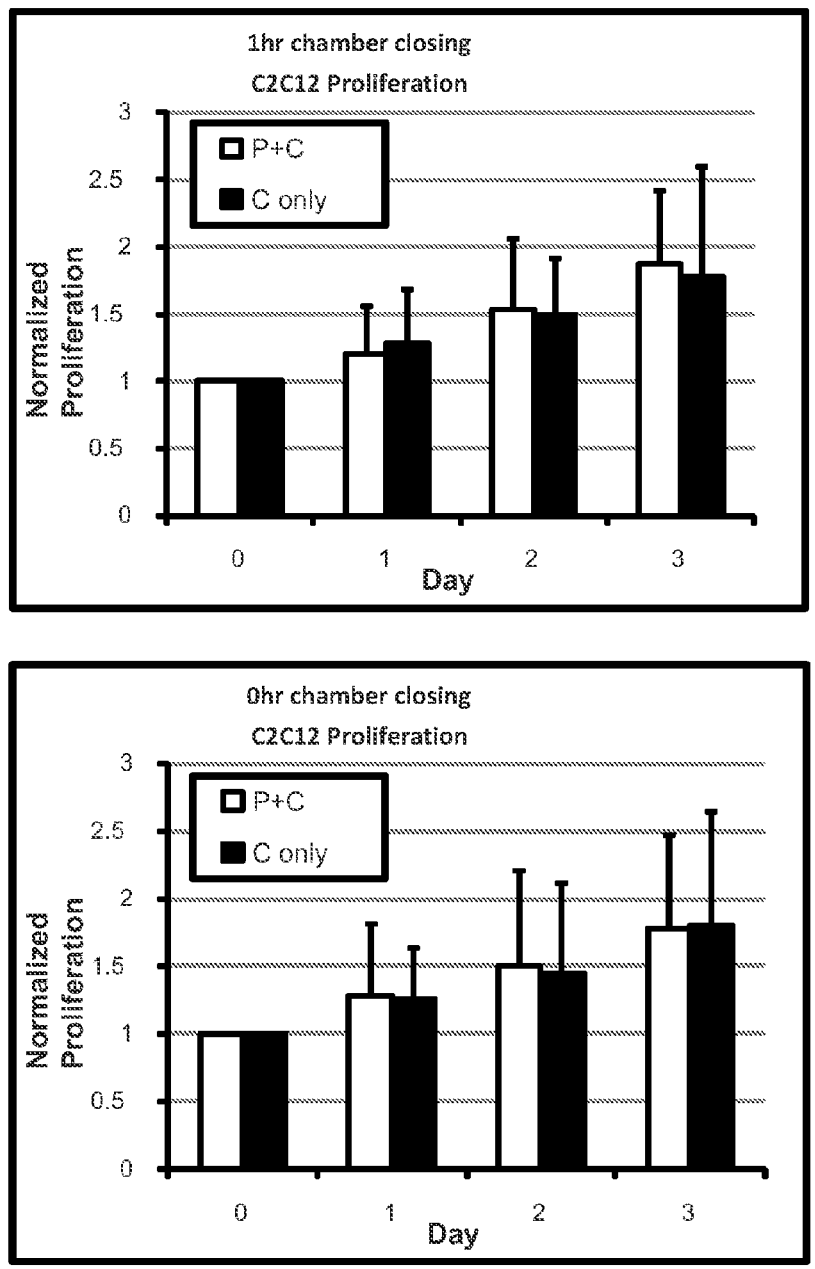
FIG. 9 depicts the results in a C2C12-PC3 co-culture without enough isolation, showing that soluble factors are not accumulated inside microchamber and do not enhance C2C12 proliferation without enough isolation.

The experiment for analyzing pairwise cell interaction was performed under low FBS (5%) conditions to monitor the effect of cell interaction rather than with other media supplements. Both C2C12 and PC3 cells were loaded in each microchamber and cultured together within specified isolation time. However, as the medium perfusion was also needed for cell culture in microfluidic environment, an attempt was made to balance the isolation and perfusion time to find the optimal cell interaction time. The culture data for cell interaction analysis between C2C12 and PC3 with different isolation time from 0 h to 3 h isolation is shown in FIGS. 8 and 9. First, the result confirms that the isolation of the cells allows them to interact with each other. Proliferation of C2C12 under the chamber interaction for 3 hours (FIG. 8) is enhanced significantly while it remained the same in 0 and 1 hour isolation as shown in FIG. 9. It is noted that there is not much difference in 1 hour chamber isolation between PC3-C2C12 and control experiment (only C2C12 cultured inside with 0 h isolation). This result can be explained by either (1) that secreted signals for 1 hour did not exceed the certain threshold level to affect C2C12 response or (2) that the signals did not diffuse enough to stimulate C2C12. Another observation is that the proliferation of C2C12 without PC3 even in 3 hour isolation was remaining in the same range with C2C12 culture in fully perfused condition. Therefore, without signals from PC3, there is no effect on the culture of C2C12 and additionally, the results of C2C12 culture without PC3 can be used as a control value.

Figure 10:
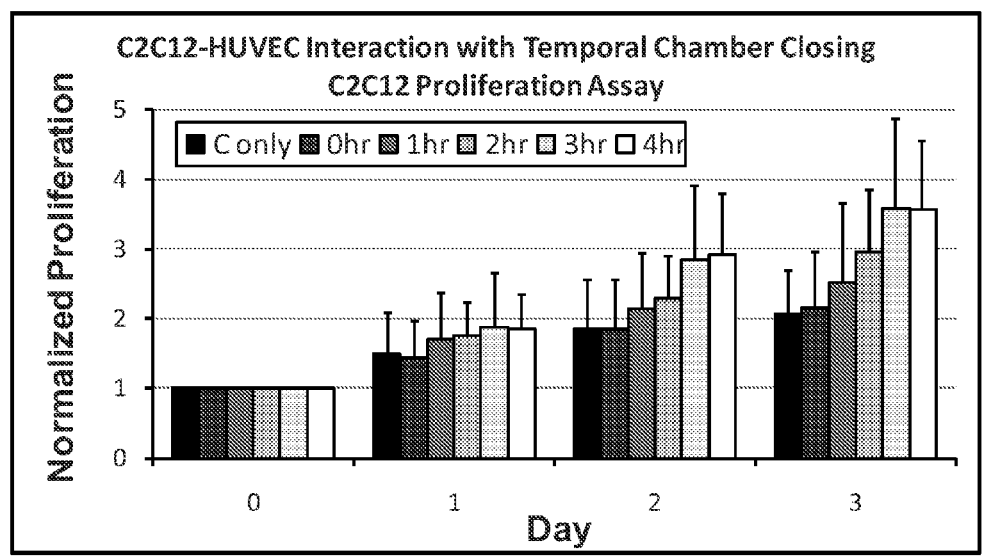
FIG. 10 is a graph of the results in a C2C12-HUVEC co-culture with isolation, showing that accumulated soluble factors from HUVEC also enhanced C2C12 proliferation.

Also, muscle satellite (stem) cells located in capillaries can be detected in many mammal species including rats, dogs and humans and separated from endothelial cells by the respective basal laminae with close proximity. There are many previous publications regarding close association between capillary and muscle satellite cells. It is well known that muscle capillary loss is associated with proportionate satellite cells decrease and its increase is associated with the increase in both satellite cells and perivascular accumulation in trained muscle. To further investigate this relationship between two types near capillaries, interaction of endothelial cells with myogenic cells using coculture is necessary. It has been partially proven that endothelial cells trigger myogenic cell growth through soluble factors (paracrine signals) and various growth factors derived from endothelial cells such as IGF-1, HGF, bFGF, PDGF-BB and VEGF. Given this, the microchamber platform described herein was used to demonstrate the interactions between myogenic cells and endothelial cells. The experimental process is identical with C2C12-PC3 experiment described above except for using HUVEC (Human Umbilical Vein Endothelial Cells) instead of PC3. For the optimal isolation conditions, various microchamber isolation time ranges (0 h~4 h) were used. FIG. 10 shows the results of C2C12-HUVEC interaction assay with different isolation time.

Figure 11:
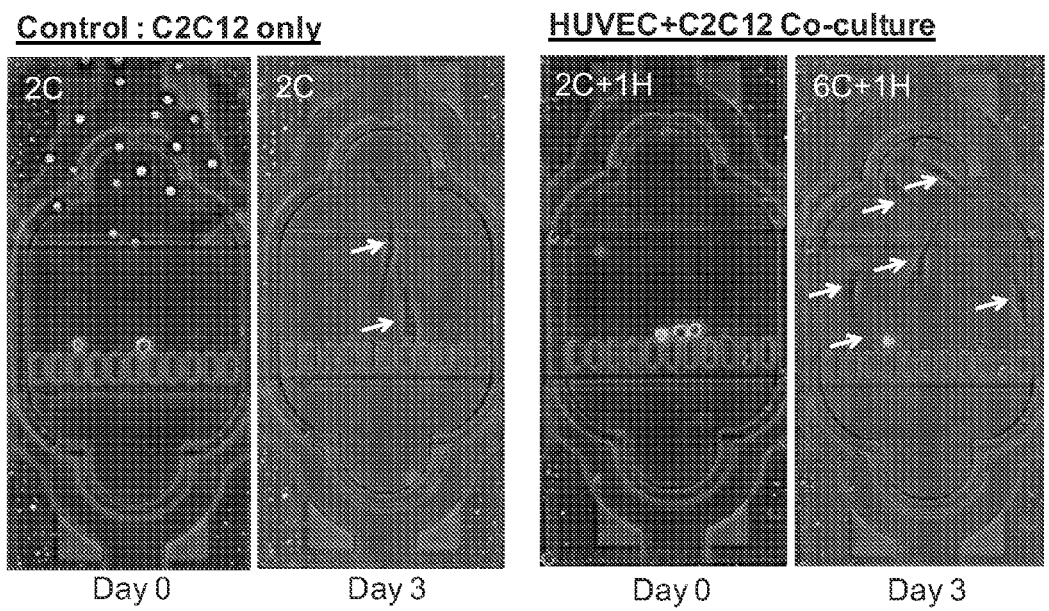
FIG. 11 depict representative images of C2C12-HUVEC co-culture under 3 hour isolation.

As with the C2C12-PC3 experiment, the optimal isolation time was determined to be 3 hours. From this result, it was concluded that the optimal isolation time, 3 hours, is more related to the features of device than to the cell's intrinsic properties and its microenvironment. Moreover, if there are significant differences in cellular metabolic process, optimal isolation time could be changed, but differences will not be significant. It was also observed that the characteristics related to interactions between C2C12-HUVEC were very similar to those of C2C12-PC3. All exhibited similar growth enhancement according to the chamber isolation time (FIG. 10). FIG. 11 shows the representative images of experimental results in pairwise cell interaction of C2C12-C2C12 and C2C12-HUVEC.

Figure 12:
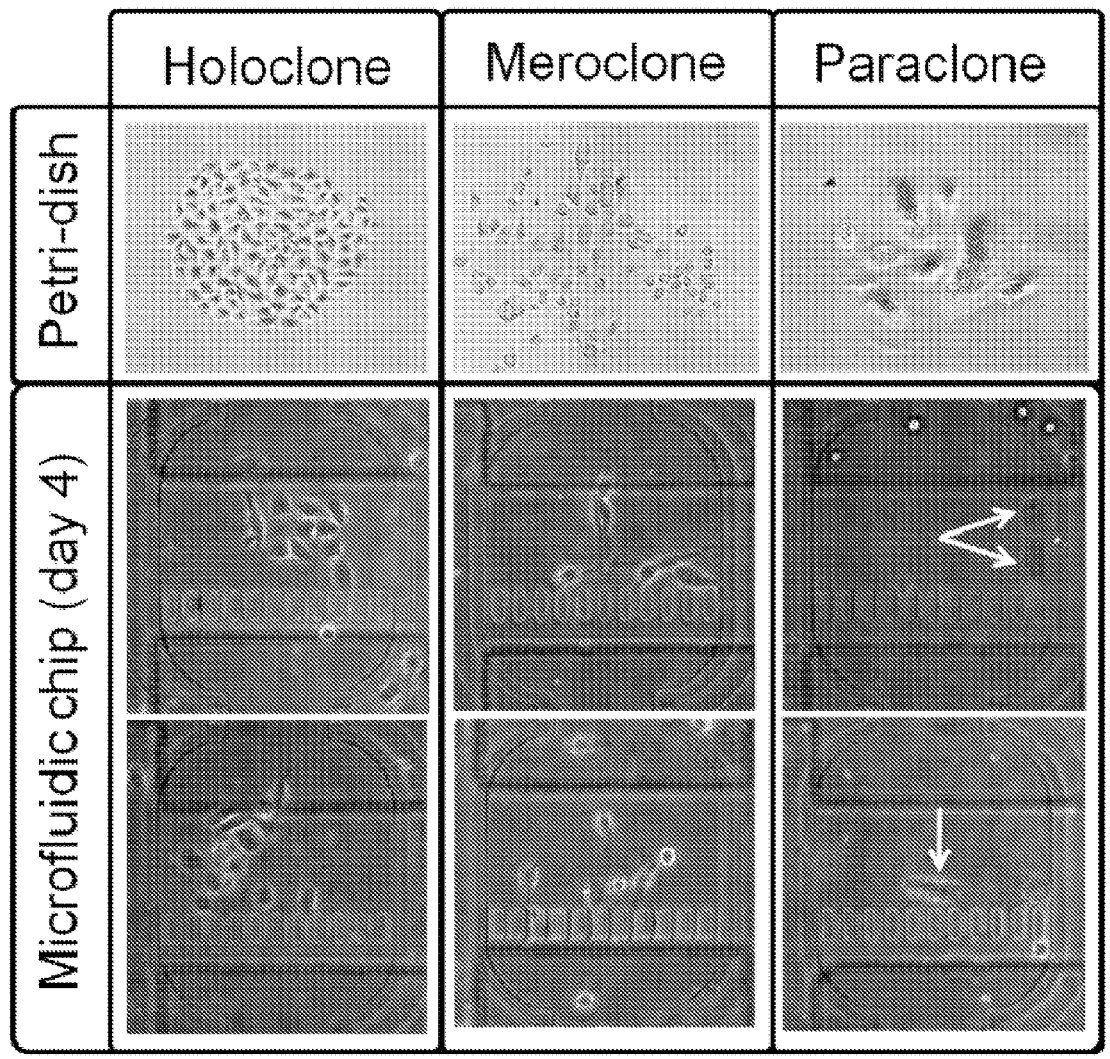
FIG. 12 depicts PC3 cultures grown in the fabricated microchambers, showing three different clonal phenotypes of PC3 cells.

Moreover, it is well-known that cancer cells and stem cells are very heterogeneous and this heterogeneity often causes mutation or differentiation into multiple different cell types among genetically identical cell population. Recently, even PC3 human prostate carcinoma cells, a cell line, gives rise to a mixture of three clonal phenotypes: holoclones, meroclones, and paraclones. The clonal culture of PC3 to identify three subclones and analyze different drug responsiveness of each subclone under microfluidic environment was investigated on the developed microfluidic device in order to demonstrate the potential of single-cell assay. FIG. 12 shows the results of clonal culture of PC3. Pure colonies of the three known clonal phenotypes of PC3 were observed and the experiment successfully demonstrated the capability for single-cell culture in the microchamber device disclosed herein.

Figure 13:
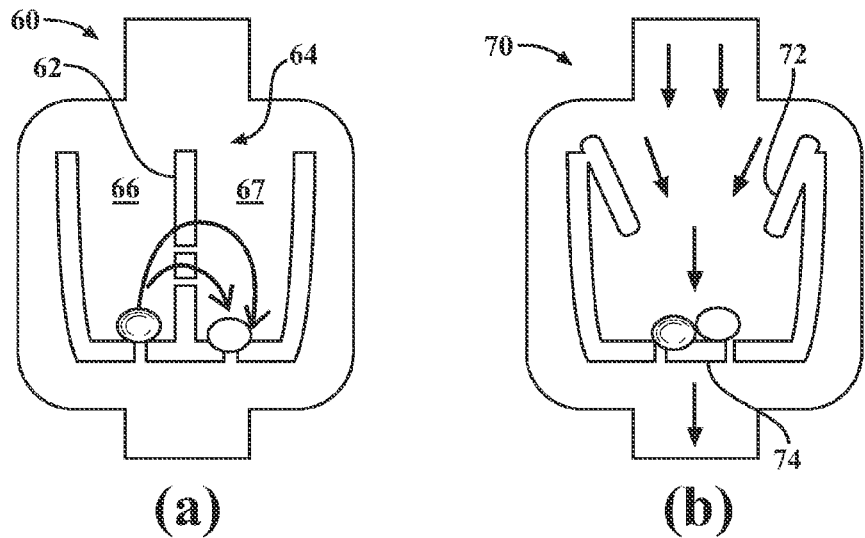
FIG. 13 depicts two alternative microchamber designs for use with non-contact secretion studies (a) and contact-mode cell studies (b)

FIGS. 13(*a*) and (*b*) depict two other microchamber embodiments which can be used to control cell-to-cell interactions so as to either limit those interactions to secretion studies (FIG. 13(a)) or to permit cell-to-cell contact (FIG. 13(b)). The microchamber 60 of FIG. 13(a) can include an internal perfusion wall 62 that partitions the interior 64 of the microchamber 60 into two sections 66, 67 that prevent cell movement between them while permitting secreted factors to move between the partitioned sections 66, 67. The microchamber 70 of FIG. 13(b) can be as shown in FIGS. 5 and 6, and may optionally include converging guide walls 72 or other means for within the interior region for directing or guiding the admitted cells into direct contact with each other. As another example, the internal cell capture structure 74 (which can be implemented in a manner similar to the cell capture structure 38 of FIG. 5) could extend across the interior of the microchamber along a path that is concave (or has some other functionally similar shape) in the direction of perfusion to act as guide walls so that the cells tend to move towards the bottom of the concave bowl shape and into contact with each other as media is flowed through the chamber. Other variations will become apparent to those skilled in the art.

Additional tests were conducted to determine the ability to carry out both secretion-mode and contact-mode cell interactions using the microchamber designs discussed above. First, a secretion study was carried out using C2C12 myoblasts and PC3 prostate cancer cells loaded into fabricated microchambers of the type show in FIG. 13(a). Previous work has demonstrated the ability of PC3 to increase cell proliferation through a secreted factor. To validate the construction and use of the microchambers for contact interaction studies, C2C12 cells and bEnd (brain endothelial) cells were co-cultured. It has been shown that co-culture of these cells will increase proliferation in both cell types, and it is believed that cell-cell contact is the most important mediating factor. By subjecting them to either secretion only or contact only conditions and monitoring their proliferation, the contributing interaction type can be determined.

Figure 14:
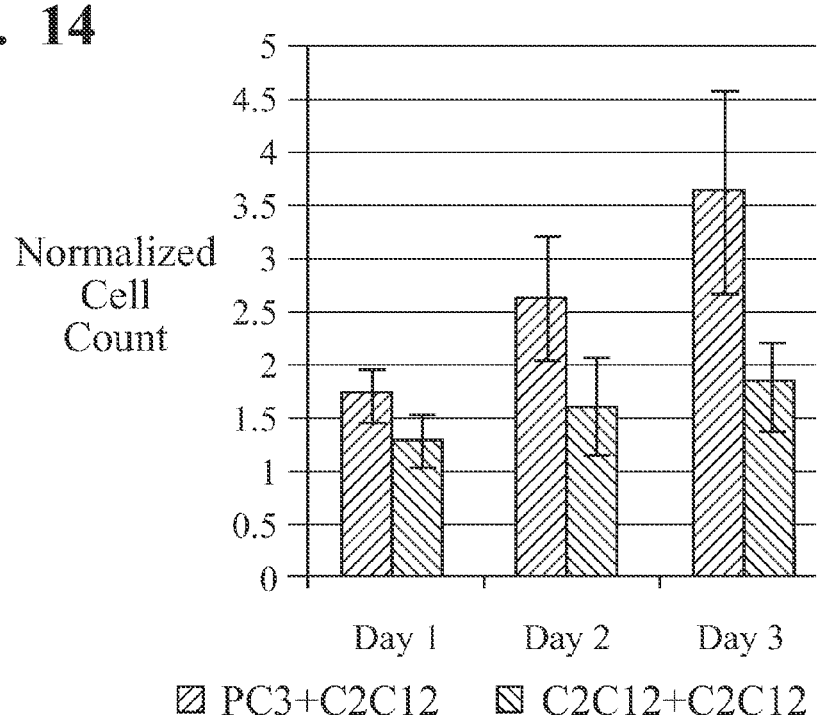
FIG. 14 is a graph showing comparative cell proliferation for C2C12+PC3 relative to a C2C12+C2C12 control using a microchamber design as in FIG. 13(a)

In the first study, PC3 cells were loaded from gravity driven wells and captured in a plurality of the microchambers 60. This process was repeated for C2C12 cells in order to capture a pair of each cell types in the microchambers. Control devices were prepared to load only two C2C12 cells instead. Both the study and control group microchambers were connected to a custom-made pneumatic controller, which closed the valves for 3 hours twice a day, and the microchambers were placed in an incubator for 3 days of cell culture. Media was continuously perfused from the inlet to the outlet but only introduced into the chambers when valves were open. Additional fresh media was added to the inlet every 20 hours. As expected, increased proliferation of C2C12 was observed only when the secreted factors from PC3 cells were allowed to accumulate, with no increase when the same cells (two C2C12 cells) were loaded, as indicated by the graphed results in FIG. 14.

By varying the isolation period and monitoring the resulting proliferation rate, the optimal isolation time has been determined. Trying times between 1 and 9 hours for 1 or 2 times per day, it was found that the twice daily, 3 hour isolation time was the optimal balance between secretion build up for stimulation and the fresh media needed for growth. This period of isolation and perfusion was used as a standard protocol for the rest of experiments for secretion based interaction studies.

Figure 15:
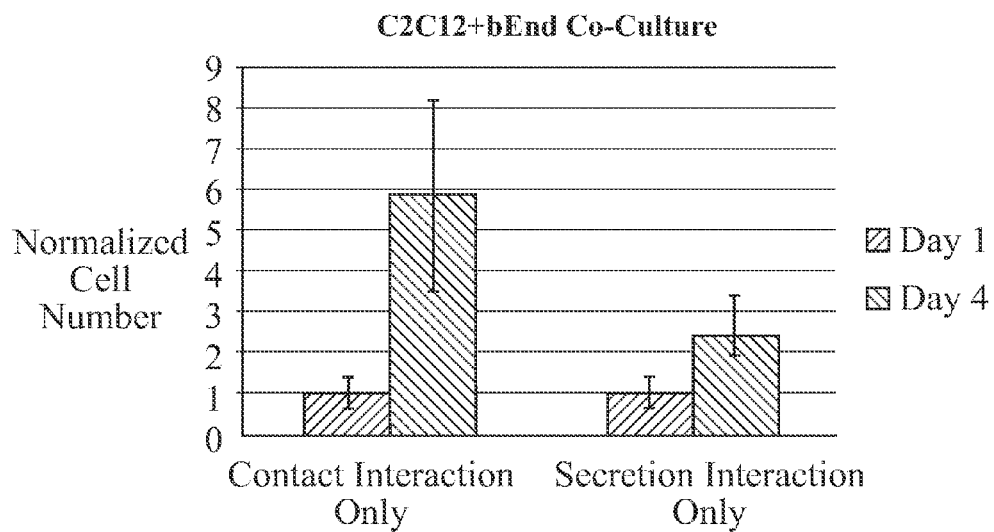
FIGS. 15 and 16 are graphs showing comparative cell proliferation of contact-mode and secretion-mode for C2C12+bEnd co-culture relative to a C2C12+10T1/2 control.
Figure 16:
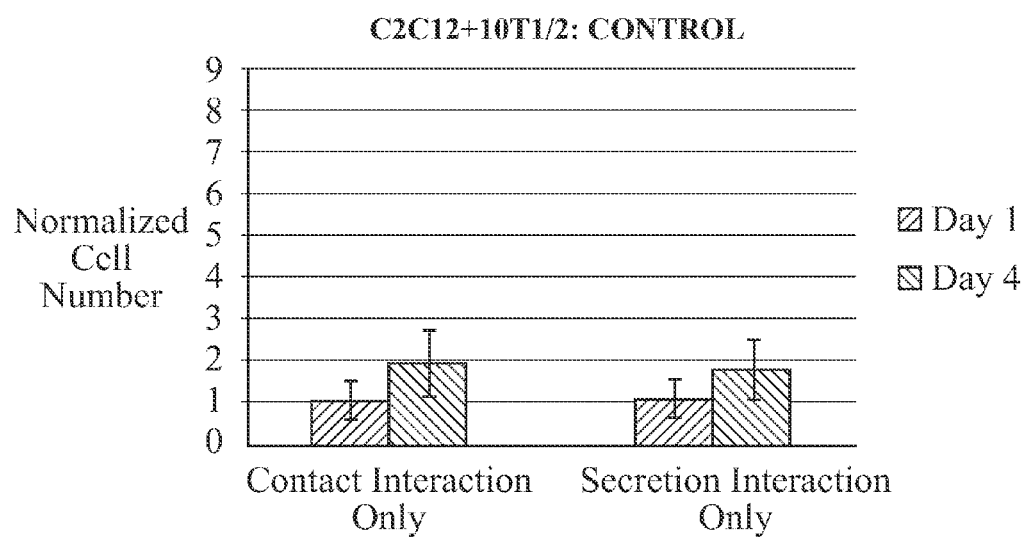

In the subsequent contact-mode cell interaction studies, C2C12 and bEnd cells were loaded pairwise into microchambers (such as in FIG. 5, 6, or 13(b)) as the positive experiment. For the control, C2C12 cells were loaded with 10T1/2 (fibroblasts) which have been previously shown not to increase C2C12 proliferation. Half of the microchambers were connected to the pneumatic actuator to be subjected to 2 separate 3 hour isolations per day, and the other half were not. In this manner, secretion-only and contact-only interactions would be distributed through the two groups of microchambers. The results are shown in FIGS. 15 and 16, and suggest that the interaction is mainly contact based and secreted factors play only a marginal role. This can be concluded from the fact that a significantly higher proliferation was observed in the continuously perfused microchambers, where cells remained in close contact. In the case that the cells were retained in separation but the secreted factors were allowed to accumulate, proliferation remained almost same and was not statistically different from that observed in the controls (both contact and secretion interactions with 10T1/2 cells).

It is to be understood that the foregoing description is of one or more preferred exemplary embodiments of the invention. The invention is not limited to the particular embodiment(s) disclosed herein, but rather is defined solely by the claims below. Furthermore, the statements contained in the foregoing description relate to particular embodiments and are not to be construed as limitations on the scope of the invention or on the definition of terms used in the claims, except where a term or phrase is expressly defined above. Various other embodiments and various changes and modifications to the disclosed embodiment(s) will become apparent to those skilled in the art. All such other embodiments, changes, and modifications are intended to come within the scope of the appended claims.

As used in this specification and claims, the terms "for example," "for instance," and "such as," and the verbs "comprising," "having," "including," and their other verb forms, when used in conjunction with a listing of one or more components or other items, are each to be construed as open-ended, meaning that the listing is not to be considered as excluding other, additional components or items. Other terms are to be construed using their broadest reasonable meaning unless they are used in a context that requires a different interpretation.

The invention claimed is:

1. A microfluidic chamber for use in individual cell assays, comprising a cell microchamber having an interior region and a front valve and a rear valve, wherein said front valve includes a cell capture site sized to retain a single cell until said front valve is opened and each of said front and rear valves is separately controllable to selectively open and close to thereby permit the transference of the single cell into and out of said interior region.

2. A microfluidic chamber as defined in claim 1, wherein said valves are controlled by pneumatic activation.

3. A microfluidic chamber as defined in claim 1, wherein said valves have a neutral position between said open and closed positions, said neutral position permitting fluid flow into and out of said cell chamber while preventing cell transference to or from said cell chamber.

4. A microfluidic chamber as defined in claim 3, wherein said front valve comprises a sidewall section that, when said front valve is in said neutral position, forms an opening having a height that is at a maximum at a center point of said front valve and that tapers down to zero at opposite ends of said front valve.

5. A microfluidic chamber as defined in claim 1, further comprising a cell capture structure within said interior region at a location between said front and rear valves, said cell capture structure permitting fluid flow through said cell capture structure while preventing movement of individual cells past said cell capture structure.

6. A microfluidic chamber as defined in claim 1, further comprising an internal perfusion wall that partitions said interior region into two sections that prevent cell movement between the two sections while permitting perfusion between the two sections.

7. A microfluidic chamber as defined in claim 1, further comprising internal guide walls located at said interior region to direct cells admitted through said front valve into direct contact with each other.

8. A microfluidic chip comprising:
a substrate; and
an array of the microfluidic chambers of claim 1 disposed on said substrate, wherein the front valves of the microchambers are interconnected to each other for simultaneous activation, and the rear valves of the microchambers are interconnected to each other for simultaneous activation.

9. A microfluidic chamber for use in individual cell assays, comprising:
a substrate;
a chamber upper wall spaced from said substrate and at least partially defining an interior region;
a chamber sidewall structure including at least one sidewall extending downwardly from said upper wall toward said substrate so as to at least partially define the interior region, said chamber upper wall and chamber sidewall structure together comprising a cell microchamber attached to said substrate;
a front valve and a rear valve, wherein said front valve comprises a first actuator and a first section of said sidewall structure located at a fluid entry point for said microchamber and includes a cell capture site sized to retain a single cell until said front valve is opened, and wherein said rear valve comprises a second actuator and a second section of said sidewall structure located at a fluid exit point for said microchamber, each of said valves being controlled via its associated actuator to permit said valves to be switched between open, neutral, and closed positions, with the neutral position for each valve permitting fluid flow through the valve while preventing cell transference through the valve, the open position for each valve permitting fluid flow and cell transference through the valve, and the closed position preventing both fluid flow and cell transference through the valve.

10. A microfluidic chamber as defined in claim 9, wherein said substrate is a glass plate.

11. A microfluidic chamber as defined in claim 9, wherein said chamber sidewall structure extends from said upper wall to said substrate such that said microchamber is sealed at all locations except said front and rear valves.

12. A microfluidic chamber as defined in claim 11, wherein said first section of said sidewall structure comprises a sidewall section that, when said front valve is in said neutral position, extends downwardly from said upper wall to a location that is spaced from said substrate by an amount that varies from a maximum spacing at a center point of said front valve down to zero at opposite ends of said front valve where said sidewall structure contacts said substrate.

13. A microfluidic chamber as defined in claim 12, wherein said maximum spacing is about 5 microns.

14. A microfluidic chamber as defined in claim 9, wherein said upper wall is flexible and wherein said actuators comprise a fluid chamber located above said upper wall at the fluid entry and exit points.

15. A microfluidic chamber as defined in claim 14, wherein said fluid chambers comprise air chambers connected to a controllable pneumatic source such that said air chambers can be selectively pressurized to thereby place said valves in said closed position or partially evacuated to thereby place said valves in said open position.

16. A microfluidic chamber as defined in claim 9, further comprising an internal perfusion wall that partitions said interior region into two sections that prevent cell movement between the two sections while permitting perfusion between the two sections.

17. A microfluidic chamber as defined in claim 9, further comprising internal guide walls located at said interior region to direct cells admitted through said front valve into direct contact with each other.

* * * * *